United States Patent
Berti et al.

(10) Patent No.: US 10,172,928 B2
(45) Date of Patent: Jan. 8, 2019

(54) PURIFICATION OF STREPTOCOCCAL CAPSULAR POLYSACCHARIDE

(71) Applicant: GLAXOSMITHKLINE BIOLOGICALS SA, Rixensart (BE)

(72) Inventors: Francesco Berti, Siena (IT); Paolo Costantino, Siena (IT); Maria Rosaria Romano, Siena (IT)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 15/536,132

(22) PCT Filed: Dec. 17, 2015

(86) PCT No.: PCT/EP2015/080228
§ 371 (c)(1),
(2) Date: Jun. 15, 2017

(87) PCT Pub. No.: WO2016/097147
PCT Pub. Date: Jun. 23, 2016

(65) Prior Publication Data
US 2017/0348408 A1   Dec. 7, 2017

(30) Foreign Application Priority Data
Dec. 19, 2014   (EP) ..................... 14199441

(51) Int. Cl.
*G01N 1/18* (2006.01)
*A61K 39/09* (2006.01)
*C08B 37/00* (2006.01)

(52) U.S. Cl.
CPC ........ *A61K 39/092* (2013.01); *C08B 37/0003* (2013.01); *C08B 37/006* (2013.01); *C08B 37/0063* (2013.01)

(58) Field of Classification Search
CPC .................................................. A61K 39/092
See application file for complete search history.

(56) References Cited

U.S. PATENT DOCUMENTS

| | | | | |
|---|---|---|---|---|
| 5,618,418 A | * | 4/1997 | Demmer | B01D 15/00 210/232 |
| 2007/0154492 A1 | * | 7/2007 | Michon | A61K 39/092 424/234.1 |
| 2011/0033554 A1 | * | 2/2011 | Burnouf | A61K 35/16 424/529 |

FOREIGN PATENT DOCUMENTS

| WO | 39/32653 | 7/1999 | |
| WO | WO 99/32653 | * 7/1999 | ............. C12P 19/04 |
| WO | 2006/082527 | 8/2006 | |
| WO | 2009/081276 | 7/2009 | |

* cited by examiner

*Primary Examiner* — Albert M Navarro (57) ABSTRACT

A purification method for the capsular polysaccharide of type II GBS in which the capsular polysaccharide is filtered using a membrane with a cut-off of less than 30 kDa.

16 Claims, 2 Drawing Sheets

PURIFICATION OF STREPTOCOCCAL CAPSULAR POLYSACCHARIDE

This application is filed pursuant to 35 U.S.C. § 371 as a United States National Phase Application of International Patent Application Serial No. PCT/EP2015/080228 filed Dec. 17, 2015, which claims priority to European Application No. 14199441.8 filed Dec. 19, 2014, and the entire contents of each of the foregoing applications are hereby incorporated by reference.

TECHNICAL FIELD

This invention is in the field of purifying bacterial capsular polysaccharides, particularly those of *Streptococcus agalactiae*, and particularly for use in the preparation of vaccines.

BACKGROUND ART

Capsular polysaccharides are important immunogens found on the surface of bacteria involved in various bacterial diseases. This feature has led to them being an important component in the design of vaccines. They have proved useful in eliciting immune responses especially when linked to carrier proteins (Ref. [1]).

Reference [2] describes a method for preparing capsular polysaccharides, particularly from *Streptococcus agalactiae* (also referred to as Lancefield's Group B *Streptococcus*, or GBS). The method comprises: (a) providing a crude isolate containing the capsular polysaccharide; (b) removing an alcohol precipitate formed by contacting the crude isolate with an alcohol solution; (c) ultrafiltration using a cellulose membrane having a cut-off of about 30 kDa to remove smaller molecular weight components while retaining the capsular polysaccharide; (d) removing protein contaminants with a protein adherent filter; (e) re-N-acetylating the purified capsular polysaccharide; and (f) ultrafiltration using a cellulose membrane having a cut-off of about 30 kDa again.

SUMMARY OF THE INVENTION

The inventor(s) purified type II GBS capsular polysaccharide according to the method of Ref. Error! Bookmark not defined, and found that the method only provided a <50% yield. Therefore, there is a need for an improved purification method that will produce a higher yield of capsular polysaccharide, in particular for type II GBS capsular polysaccharide.

The invention is based on the finding that a membrane with a cut-off of 10 kDa compared to 30 kDa in step (f) of Ref. Error! Bookmark not defined, gives a higher yield, e.g. about 90%. Without wishing to be bound by theory, the increase in yield seems to be caused by a more linear conformation of type II GBS capsular polysaccharide compared to the other GBS capsular polysaccharides (e.g. from types Ia, Ib, III and V). The more linear conformation results in reduced steric hindrance and a lower hydrodynamic radius, which means that the polysaccharide is prone to loss through a membrane with a higher molecular weight cut-off.

The inventors have also found that good yields of type II GBS capsular polysaccharide can be obtained with a method that does not require a chromatography step and, in particular, does not require hydrophobic-interaction chromatography (HIC).

Thus, the invention provides a method for purifying a type II GBS capsular polysaccharide, comprising a filtration step that uses a membrane with a cut-off of less than about 30 kDa.

The invention also provides, in a method for purifying a type II GBS capsular polysaccharide, the improvement consisting of the use of a membrane with a molecular weight cut-off of less than about 30 kDa for a filtration step, in place of a membrane with a molecular weight cut-off of about 30 kDa.

The filtration step may use a membrane with a ≤25 kDa cut-off, e.g. ≤20 kDa, ≤15 kDa or ≤10 kDa. Preferably, the filtration step uses a membrane with a 10 kDa cut-off.

The filtration step is discussed in more detail below.

Typically, one or more additional steps are performed before the filtration step. Suitable steps include: (a) providing a crude isolate containing the capsular polysaccharide; (b) removing an alcohol precipitate formed by contacting the crude isolate with an alcohol solution; and (c) removing protein contaminants with a protein adherent filter.

In certain embodiments, one or more additional steps may be performed after the filtration step. For example, the additional steps may be: (e) precipitating the purified capsular polysaccharide; (f) conjugating the capsular polysaccharide to a carrier protein, e.g. diphtheria toxoid, tetanus toxoid or $CRM_{197}$; (g) formulating a vaccine with the capsular polysaccharide as a component; and/or (h) mixing with one or more capsular polysaccharide(s) from a GBS serotype selected from the group consisting of: Ia, Ib, III, IV, V, VI, VII and VIII, particularly wherein these capsular polysaccharide(s) are conjugated to carrier protein(s), e.g. diphtheria toxoid, tetanus toxoid or $CRM_{197}$.

The method may comprise more than one filtration steps. In which case, it is typically the final filtration step that uses a membrane with a cut-off of less than about 30 kDa.

The invention also provides a composition comprising a type II GBS capsular polysaccharide, obtainable by the purification method of the invention.

DETAILED DESCRIPTION OF PREFERRED EMBODIMENTS

The Capsular Saccharide

GBS-related disease arises primarily from serotypes Ia, Ib, II, III, IV, V, VI, VII, and VIII, with over 90% being caused by five serotypes: Ia, Ib, II, III & V. The *S. agalactiae* capsular polysaccharide is covalently linked to GlcNAc residues in the bacterium's peptidoglycan backbone, and is distinct from the group B antigen, which is a separate saccharide that is attached to MurNAc residues on the same peptidoglycan backbone [3]. The capsular polysaccharides of different serotypes are chemically related, but are antigenically very different. All GBS capsular polysaccharides share the following trisaccharide core:

β-D-GlcpNAc(1→3)β-D-Galp(1→4)β-D-Glcp

The various GBS serotypes differ by the way in which this core is modified.

The invention uses GBS that belong to serotype II. Preferably the invention uses any type II GBS strain that expresses a reasonable amount of capsule polysaccharide to complete for purification, e.g. 18RS21 or DK21.

Figure 1:
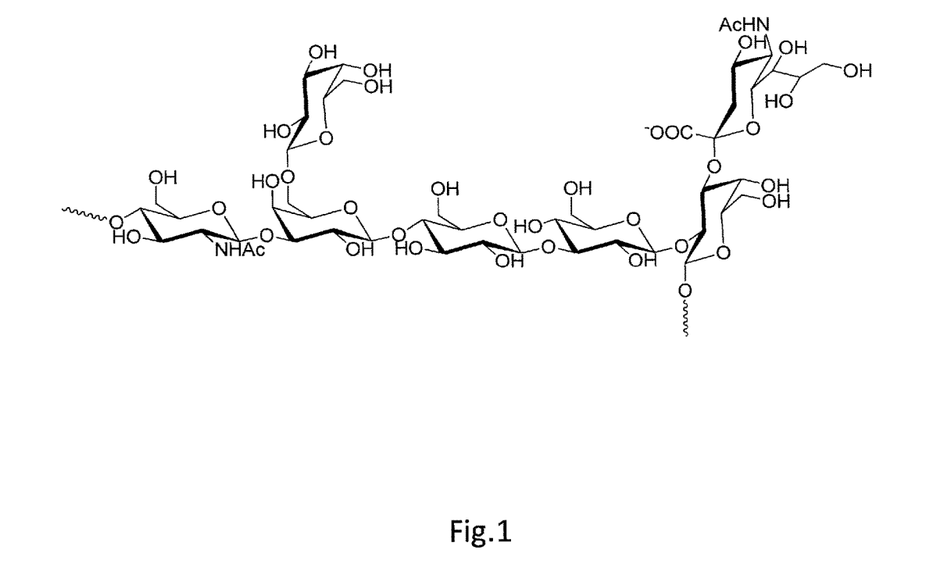
FIG. 1 shows the molecular structure of serotype specific capsular polysaccharide from type II GBS.

As shown in FIG. 1, the capsular saccharide of type II GBS includes: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core. Type II GBS capsular polysaccharide's trisaccharide core contains three galactose residues per repeating unit.

Saccharides purified according to the invention will generally be in their native form, but they may have been modified. For example, the saccharide may be shorter than the native capsular saccharide, or may be chemically modified. For instance, it may be modified to produce non-natural capsular polysaccharides or heterologous polysaccharides or to increase yield.

Thus the saccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. Chain length has been reported to affect immunogenicity of GBS saccharides in rabbits [4].

The saccharide may be chemically modified relative to the capsular saccharide as found in nature. For example, the saccharide may be de-O-acetylated (partially or fully), de-N-acetylated (partially or fully), N-propionated (partially or fully), etc. Depending on the particular saccharide, de-acetylation may or may not affect immunogenicity e.g. the NeisVac-C™ vaccine uses a de-O-acetylated saccharide, whereas Menjugate™ is acetylated, but both vaccines are effective. The relevance of O-acetylation on GBS saccharides in various serotypes is discussed in reference [5], and it is preferred to retain O-acetylation of sialic acid residues at positions 7, 8 and/or 9 before during and after purification e.g. by using formaldehyde for extraction of the saccharide and/or bacterial inactivation, by protection/de-protection, by re-acetylation, etc. The effect of de-acetylation etc. can be assessed by routine assays.

Purification Method

The purification method typically contains multiple steps, as explained further below. The steps typically take place in the order described below, although other orders may also be effective.

Starting Material

Methods for preparing capsular saccharides from bacteria are well known in the art, e.g., see references [6-8], etc. For GBS, the following methods may be used (see also Ref. [9]). The purification method of the invention may start with a crude isolate containing the type II GBS capsular polysaccharide. The capsular saccharide is in aqueous form, typically as a suspension comprising streptococcal proteins, nucleic acids and capsular polysaccharide.

Generally, a small amount of capsular polysaccharide is released into the culture medium during bacterial growth, and so the starting material for alcoholic precipitation of contaminating proteins and/or nucleic acids may thus be the supernatant from a centrifuged bacterial culture. For example, in certain embodiments, the polysaccharide may be isolated from Streptococcus agalactiae bacteria that comprise mutations in cpsA (uniprot accession number Q9RPC7) and/or cpsD (uniprot accession number K0JNC2) and secrete large quantities of capsular polysaccharide into the culture medium. Suitable mutants and mutations are disclosed in International Patent Application No. PCT/EP2015/059773 (published as WO2015/169774), herein incorporated by reference. More typically, however, the starting material will be prepared by treating the capsulated bacteria themselves (or material containing the bacterial peptidoglycan), such that the capsular saccharide is released.

Capsular polysaccharide can be released from bacteria by various methods, including chemical, physical or enzymatic treatment. Thus an aqueous preparation of polysaccharide can be treated prior to the initial protein/nucleic acid precipitation reaction.

A typical chemical treatment is base extraction [10] (e.g. using sodium hydroxide), which can cleave the phosphodiester linkage between the capsular saccharide and the peptidoglycan backbone. Base extraction is advantageous because it inactivates the bacteria at the same time as releasing the capsular polysaccharide. Moreover, base treatment releases the polysaccharide intact and causes extensive cleavage of the group B antigen due to its multiple phosphodiester linkages [3], facilitating later separation of the capsular and group-specific saccharide antigens. Sodium hydroxide treatment is therefore a preferred method for releasing the capsular polysaccharide. The inventors found that a sodium hydroxide treatment using 0.8M NaOH at 37° C. for 36 hours is particularly useful with the method of the invention. As hydroxide treatment de-N-acetylates the capsular saccharide, however, later re-N-acetylation may be useful.

A typical enzymatic treatment involves the use of both mutanolysin and β-N-acetylglucosaminidase [3]. These act on the GBS peptidoglycan to release the capsular saccharide for use with the invention, but also lead to release of the group-specific carbohydrate antigen. An alternative enzymatic treatment involves treatment with a type II phosphodiesterase (PDE2). PDE2 enzymes can cleave the same phosphates as sodium hydroxide (see above) and can release the capsular saccharide without cleaving the group-specific carbohydrate antigen and without de-N-acetylating the capsular saccharide, thereby simplifying downstream steps. PDE2 enzymes are therefore a preferred option for preparing GBS capsular saccharides for use in the method of the invention.

A preferred starting material for the method of the invention is thus de-N-acetylated capsular polysaccharide, which can be obtained by base extraction as described in reference [10]. Another preferred starting material is thus the product of PDE2 treatment of GBS. Such materials can be subjected to concentration (e.g. ultrafiltration) prior to precipitation by the method of the invention.

Alcoholic Precipitation and Cation Exchange

The type II GBS capsular saccharide obtained after culture will generally be impure and will be contaminated with bacterial nucleic acids and proteins. The method of the invention may utilise alcoholic precipitation. If necessary (e.g. after base extraction), materials will usually be neutralised prior to the precipitation.

The alcohol used to precipitate contaminating nucleic acids and/or proteins is preferably a lower alcohol, such as methanol, ethanol, propan-1-ol, propan-2-ol, butan-1-ol, butan-2-ol, 2-methyl-propan-1-ol, 2-methyl-propan-2-ol, diols, etc. The selection of an appropriate alcohol can be tested empirically, without undue burden, but alcohols such as ethanol and isopropanol (propan-2-ol) are preferred, rather than alcohols such as phenol.

The alcohol is preferably added to the polysaccharide suspension to give a final alcohol concentration of between 10% and 50% (e.g. around 30%). The most useful concentrations are those which achieve adequate precipitation of contaminants without also precipitating the polysaccharide.

The optimum final alcohol concentration may depend on the GBS strain from which the polysaccharide is obtained, and can be determined by routine experiments without undue burden. Precipitation of polysaccharides at ethanol concentrations >50% has been observed.

In certain embodiments the alcohol solution is added to a concentration sufficient to precipitate nucleic acid contaminants but not the capsular polysaccharide. In preferred embodiments, the alcohol is ethanol preferably added to a concentration of between about 10% and about 50% ethanol, more preferably to a concentration of about 30% ethanol. The inventors found that an alcoholic precipitation step that involves adding ethanol to a concentration of between 30% ethanol is particularly useful with the method of the invention.

The alcohol solution may optionally include a cation, preferably a metal cation, more preferably a divalent cation, most preferably calcium.

The alcohol may be added in pure form or may be added in a form diluted with a miscible solvent (e.g. water). Preferred solvent mixtures are ethanol:water mixtures, with a preferred ratio of between around 70:30 and around 95:5 (e.g. 75:25, 80:20, 85:15, 90:10).

The saccharide is also treated with an aqueous metal cation. Monovalent and divalent metal cations are preferred, and divalent cations are particularly preferred, such as $Mg^{++}$, $Mn^{++}$, $Ca^{++}$, etc, as they are more efficient at complex formation. Calcium ions are particularly useful, and so the alcohol mixture preferably includes soluble calcium ions. These may be added to a saccharide/alcohol mixture in the form of calcium salts, either added as a solid or in an aqueous form. The calcium ions are preferably provided by the use of calcium chloride.

The calcium ions are preferably present at a final concentration of between 10 and 500 mM e.g. about 0.1 M. The optimum final $Ca^{++}$ concentration may depend on the GBS serotype from which the polysaccharide is obtained, and can be determined by routine experiments without undue burden.

The alcohol and the cation play different roles (the alcohol is used to precipitate contaminants, whereas the cation stabilises and complexes the saccharide in soluble form) but produce a combined effect. Although the aim is to prepare a mixture of the saccharide, the alcohol and the cation, these three components need not be mixed together simultaneously. Thus the alcohol and cation can be used sequentially or simultaneously. Sequential treatment is preferred, and a particularly preferred method involves addition of the cation to the saccharide followed by addition of the alcohol to the cation/saccharide mixture, although the alcohol can be used before the cation if desired.

After alcoholic precipitation of contaminating proteins and/or nucleic acids, the GBS capsular polysaccharide is left in solution. The precipitated material can be separated from the polysaccharide by any suitable means, such as by centrifugation. The supernatant can be subjected to microfiltration, and in particular to dead-end filtration (perpendicular filtration) in order to remove particles that may clog filters in later steps (e.g. precipitated particles with a diameter greater than 0.22 µm). As an alternative to dead-end filtration, tangential microfiltration can be used.

Filtration Step

The invention involves a filtration step using a membrane with a cut-off of less than about 30 kDa. The method may use a membrane with a ≤25 kDa cut-off, e.g. ≤20 kDa, ≤15 kDa or ≤10 kDa. Preferably, the filtration step uses a membrane with a with a 10 kDa cut-off. The filtration membrane allows passage of hydrolysis products while retaining the capsular polysaccharide.

The invention may use more than one filtration steps. For example, the method may comprise: (i) one or more (e.g. 2, 3, 4, 5, 6, etc.) filtration steps after the alcoholic precipitation and cation exchange step described above and before the filtration with a protein adherent filter described below, and (ii) a filtration step after the filtration with a protein adherent filter, wherein the filtration step in (ii) is the one that uses a membrane with a cut-off of less than about 30 kDa. Alternatively, all of the filtration steps use a membrane with a cut-off of less than about 30 kDa, particularly ≤10 kDa.

In at least one filtration step in the invention (typically the final filtration step, e.g. in step (ii) above), the membrane of the filtration step has a cut-off of less than about 30 kDa (e.g. ≤25 kDa, ≤20 kDa, ≤15 kDa or ≤10 kDa). In the other filtration steps (e.g. in step (i) above), a cut-off in the range of about 10 kDa-30 kDa may be useful. Smaller cut-off sizes can be used, as the hydrolysis fragments of the group-specific antigen are generally around 1 kDa (5-mer, 8-mer and 11-mer saccharides), but the higher cut-off advantageously allows removal of other contaminants without leading to loss of the capsular saccharide.

The invention may be a method comprising more than one filtration steps, and the filtration step that uses a membrane with a cut-off of less than about 30 kDa is the final filtration step. The method may comprise more than two filtration steps, and the filtration step that uses a membrane with a cut-off of less than about 30 kDa is the final filtration step. In particular, the final filtration step may use a membrane with a cut-off of about 10 kDa. In particular, the method may comprise: (i) a filtration step that uses a membrane with a cut-off of less than about 30 kDa; (ii) a further filtration step that uses a membrane with a cut-off of less than about 30 kDa; and (iii) a further filtration step that uses a membrane with a cut-off of about 10 kDa.

In particular the invention may be a method comprising one or more, or all of the following steps: (i) a filtration step that uses a ≤0.65 µm membrane; (ii) a filtration step that uses a membrane with a cut-off of less than about 30 kDa; (iii) a filtration step that uses a 0.45-0.22 µm membrane; (iv) a filtration step that uses a membrane with a cut-off of less than about 30 kDa; (v) a filtration step that uses a protein adherent filter; (vi) a filtration step that uses a membrane with a cut-off of about 10 kDa; (vii) a filtration step that uses a 0.22 µm disposable syringe filter.

The filtration step may be an ultrafiltration step. Ultrafiltration is a separation process whereby solvent is removed from a solution (including a colloidal solution) or a suspension by forcing it to flow through a membrane by the application of a hydraulic pressure. Components in the solution which are significantly larger than the pores in the membrane cannot pass through the membrane.

The ultrafiltration is preferably cross flow or tangential flow ultrafiltration. In tangential flow ultrafiltration, the solution flows substantially parallel to the membrane surface, rather than flowing perpendicular to the surface as in ordinary filtration. Tangential flow diafiltration is typical.

The ultrafiltration step preferably results in diafiltration of the solution. In diafiltration, solvent and/or microsolutes (e.g. salts) which are removed during ultrafiltration are replaced by new solvent and microsolutes. In general, removal and replacement occur at the same rate and the volume of the solution is thus kept constant. The overall effect of the process is therefore the replacement of original solvent/microsolutes with new solvent/microsolutes. The new solvent/microsolutes may be any suitable buffer, e.g. a Tris buffer, a NaPi buffer or a Na$_2$CO$_3$ buffer.

Typically, each diafiltration step replaces the buffer with a different buffer. For example, where the method of the invention involves using two or more diafiltration steps, e.g. (i) one or more (e.g. 2, 3, 4, 5, 6, etc.) diafiltration steps after the alcoholic precipitation and cation exchange step described above and before the filtration with a protein adherent filter described below, and (ii) a diafiltration step after the filtration with a protein adherent filter, the diafiltration step(s) in (1) replace the buffer (e.g. a Tris buffer) with a different buffer (e.g. a NaPi buffer), and the diafiltration step in (ii) replaces the buffer (e.g. a NaPi buffer) with another buffer (e.g. KPi buffer). Preferably, the diafiltration step(s) in (i) use a membrane with a cut-off of about 30 kDa, and the diafiltration step in (ii) uses a membrane with a cut-off of less than about 30 kDa (e.g. ≤25 kDa, ≤20 kDa, ≤15 kDa or ≤10 kDa).

In some embodiments, step (i) comprises two diafiltration steps. In which case, the first diafiltraion step replaces the buffer (e.g. a Tris buffer) with a different buffer (e.g. a NaPi buffer) and the second diafiltration step replaces the buffer (e.g. a NaPi buffer) with another buffer (e.g. a Na$_2$CO$_3$ buffer). Preferably, both diafiltration steps in (i) use a membrane with a cut-off of about 30 kDa, and the diafiltration step in (ii) uses a membrane with a cut-off of less than about 30 kDa (e.g. ≤25 kDa, ≤20 kDa, ≤15 kDa or ≤10 kDa).

At least 5 cycles of diafiltration are usually performed e.g. 6, 7, 8, 9, 10, 11, 12, 13, 14, 15, 16 or more. The number of cycles of diafiltration may differ at different diafiltration steps. For example, where the method of the invention involves using two or more diafiltration steps, e.g. (i) one or more (e.g. 2, 3, 4, 5, 6, etc.) diafiltration steps after the alcoholic precipitation and cation exchange step described above and before the filtration with a protein adherent filter described below, and (ii) a diafiltration step after the filtration with a protein adherent filter, the numbers of cycles of diafiltration (i) and (ii) may be different. For example, the invention may use x number of cycles in the diafiltration step in (i), and y number of cycles in the diafiltration step in (ii), x and y may independently be ≥5, e.g. 6, 7, 8, 9, 10, 11, 12, 13, 14, 15, 16 or more. Preferably, x≤y. Preferably, x=6 and y=16. Preferably, the diafiltration step in (i) uses a membrane with a cut-off of about 30 kDa, and the diafiltration step in (ii) uses a membrane with a cut-off of less than about 30 kDa (e.g. ≤25 kDa, ≤20 kDa, ≤15 kDa or ≤10 kDa).

A diafiltration step preferably lasts less than 10 hours e.g. between 2 and 6 hours, preferably between 3 and 5 hours e.g. between 3.5 and 4.5 hours.

Filtration membranes may be made from any suitable material e.g. cellulose, polyethersulphone or regenerated cellulose membranes.

Preferably, the final filtration step of the method of the invention is an ultrafiltration step that results in diafiltration and that uses a cellulose membrane with a cut-off of 10 kDa.

Filtration with a Protein Adherent Filter

The purification of the capsular polysaccharides may further include a step whereby protein and/or DNA contaminants are removed by filtration with a filter, e.g. a protein adherent filter, to which protein and/or DNA adheres, but to which the capsular polysaccharide does not adhere or only weakly adheres.

The protein adherent filter typically comprises activated carbon (e.g. as a granular carbon bed or as a pressed or extruded carbon block), which acts as the filter for purification of the sample. Typically, a carbon filter for use in the present invention contains activated carbon immobilized in a matrix. The matrix may be any porous filter medium permeable for the sample.

The matrix may comprise a support material and/or a binder material. The support material may be a synthetic polymer or a polymer of natural origin. Suitable synthetic polymers may include polystyrene, polyacrylamide and polymethyl methacrylate, while polymers of natural origin may include cellulose, polysaccharide and dextran, agarose. Typically, the polymer support material is in the form of a fibre network to provide mechanical rigidity. The binder material may be a resin. The matrix may have the form of a membrane sheet.

Typically, the activated carbon is immobilized in the matrix may be in the form of a cartridge. A cartridge is a self-contained entity containing powdered activated carbon immobilized in the matrix and prepared in the form of a membrane sheet. The membrane sheet may be captured in a plastic permeable support to form a disc. Alternatively, the membrane sheet may be spirally wound. To increase filter surface area, several discs may be stacked upon each other. In particular, the discs stacked upon each other have a central core pipe for collecting and removing the carbon-treated sample from the filter. The configuration of stacked discs may be lenticular.

The activated carbon in the carbon filter may be derived from different raw materials, e.g. peat, lignite, wood or coconut shell. Any process known in the art, such as steam or chemical treatment, may be used to activate carbon.

In the present invention, activated carbon immobilized in a matrix may be placed in a housing to form an independent filter unit. Each filter unit has its own in-let and out-let for the sample to be purified. Examples of filter units that are usable in the present invention are the carbon cartridges from Cuno Inc. (Meriden, USA) or Pall Corporation (East Hill, USA).

Preferably, the invention uses CUNO zetacarbon™ filters. These carbon filters comprise a cellulose matrix into which activated carbon powder is entrapped and resin-bonded in place.

Re-N-Acetylation

When the starting material is treated with base extraction, e.g. hydroxide treatment (see above), then the method of the invention may include a N-acetylation step to re-N-acetylate the capsular saccharide.

The inventors found that a N-acetylation step that uses a stock solution of acetic anhydride at the following proportions is particularly useful with the method of the invention: 4.15 mL of acetic anhydride per L, with acetic anhydride:ethanol=1:1.

Further Treatment of the Capsular Polysaccharide

The polysaccharide may be further treated to remove contaminants. This is particularly important in situations where even minor contamination is not acceptable (e.g. for human vaccine production).

One preferred further step is a precipitation step. For example, the precipitation may use an aqueous cation solution. The precipitated saccharide can then be separated from any remaining aqueous contaminants e.g. by centrifugation. The precipitated material is stable and can be stored for future use.

The precipitating step may use AcONa. In particular, contaminants can be removed by adding 400 mM AcONa at pH 4.4 (⅕ volume). The mixture can be mixed for 15-20 minutes at room temperature and then filter sterilized using a 0.45/0.2 μm filter.

The invention may also use one or more sterile filtration steps, which typically involves filtering using a 0.65 μm-0.22 μm filter and/or a 0.45/0.2 μm filter.

The precipitated material may be subjected to vacuum drying. This treatment will typically be used not to stabilise the saccharide for storage, but to dry the saccharide and remove any residual alcohol. Further rounds of precipitation and filtration can also be performed. Depth filtration can also be used e.g. as an alternative to centrifugation. Depth filtration will typically be used after solubilisation in alcohol.

The polysaccharide may be depolymerised to form oligosaccharides, after they are prepared from the bacteria but before conjugation. Depolymerization reduces the chain length of the saccharides and may not be good for GBS. Oligosaccharides may be preferred to polysaccharides for use in vaccines, and chain length has been reported to affect immunogenicity of GBS saccharides in rabbits [4]. If depolymerisation is performed, the products will generally be sized in order to remove short-length oligosaccharides. This can be achieved in various ways, such as ultrafiltration followed by ion-exchange chromatography. Where the composition of the invention includes a depolymerised saccharide, it is preferred that depolymerisation precedes any conjugation.

If sialic acid residues in the GBS capsular saccharides have been de-N-acetylated then the method of the invention may include a step of re-N-acetylation. Controlled re-N-acetylation can conveniently be performed using a reagent such as acetic anhydride $(CH_3CO)_2O$ e.g. in 5% ammonium bicarbonate [11].

These additional steps can generally be performed at room temperature.

The inventors have found that good yields of type II GBS capsular polysaccharide can be obtained with a method that does not require a chromatography step. Thus, the method of the invention does not include a chromatography step. In particular, the method does not include a step of hydrophobic-interaction chromatography (HIC). In particular, the method does not include a step involving chromatography using phenyl sepharose.

Conjugation Preparation

The final purified capsular polysaccharide of the invention can be used as an antigen without further modification e.g. for use in in vitro diagnostic assays, for use in immunisation, etc.

For immunisation purposes, however, it is preferred to conjugate the saccharide to a carrier molecule, such as a protein. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. [12] and is a well known technique [e.g. reviewed in refs. [13-21]. Thus the method of the invention may include the further step of conjugating the purified saccharide to a carrier molecule.

Conjugation of GBS saccharides has been widely reported e.g. see references [22-28]. The typical prior art process for GBS saccharide conjugation typically involves reductive amination of a purified saccharide to a carrier protein such as tetanus toxoid (TT) or $CRM_{197}$ [23]. The reductive amination involves an amine group on the side chain of an amino acid in the carrier and an aldehyde group in the saccharide. As GBS capsular saccharides do not include an aldehyde group in their natural form then this is generated before conjugation by periodate oxidation of a portion (e.g. between 5 and 15%, preferably about 10%) of the saccharide's sialic acid residues [23, 29]. Conjugate vaccines prepared in this manner have been shown to be safe and immunogenic in humans for each of GBS serotypes Ia, Ib, II, III, and V [30]. An alternative conjugation process involves the use of $-NH_2$ groups in the saccharide (either from de-N-acetylation, or after introduction of amines) in conjunction with bifunctional linkers, as described in ref. [31].

Preferred carrier proteins are bacterial toxins or toxoids, such as diphtheria toxoid or tetanus toxoid. The $CRM_{197}$ mutant of diphtheria toxin [32-34] is a particularly preferred carrier for, as is a diphtheria toxoid. Other suitable carrier proteins include the N. meningitidis outer membrane protein [35], synthetic peptides [36-37], heat shock proteins [38-39], pertussis proteins [40-41], cytokines [42], lymphokines [42], hormones [42], growth factors [42], human serum albumin (preferably recombinant), artificial proteins comprising multiple human $CD4^+$ T cell epitopes from various pathogen-derived antigens [43] such as N19 [44], protein D from H. influenzae [45-46], pneumococcal surface protein PspA [47], pneumolysin [48], iron-uptake proteins [49], toxin A or B from C. difficile [50], a GBS protein [51], etc. Other suitable carrier proteins include C5a peptidase ("SCP") disclosed in WO2010/053986, for example, C5a peptidase from Group A Streptococcus (SCPA) or Group B Streptococcus (SCPB).

Attachment to the carrier is preferably via a $-NH_2$ group e.g. in the side chain of a lysine residue in a carrier protein, or of an arginine residue. Attachment may also be via a $-SH$ group e.g. in the side chain of a cysteine residue.

It is possible to use more than one carrier protein e.g. to reduce the risk of carrier suppression. Thus different carrier proteins can be used for different GBS serotypes e.g serotype Ia saccharides might be conjugated to $CRM_{197}$ while serotype Ib saccharides might be conjugated to tetanus toxoid. It is also possible to use more than one carrier protein for a particular saccharide antigen e.g. serotype III saccharides might be in two groups, with some conjugated to $CRM_{197}$ and others conjugated to tetanus toxoid. In other embodiments, GBS proteins such as SCPB described above, may be used either as a carrier for one or more of polysaccharide types Ia, Ib, II, III and V or as an additional protein antigen component in such a composition. In general, however, it is preferred to use the same carrier protein for all saccharides.

A single carrier protein might carry more than one saccharide antigen [52-53]. For example, a single carrier protein might have conjugated to it saccharides from serotypes Ia and Ib. To achieve this goal, different saccharides can be mixed prior to the conjugation reaction. In general, however, it is preferred to have separate conjugates for each serogroup, with the different saccharides being mixed after conjugation. The separate conjugates may be based on the same carrier.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5. Ratios between 1:1 and 4:1 are also preferred. With longer saccharide chains, a weight excess of saccharide is typical. In general, the invention provides a conjugate, wherein the conjugate comprises a Streptococcus, preferably a S. agalactiae capsular saccharide moiety joined to a carrier, wherein the weight ratio of saccharide:carrier is at least 2:1.

Conjugates may be used in conjunction with free carrier [54]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalized prior to conjugation. Activation may involve, for example, cyanylating reagents such as CDAP (e.g., 1.-cyano-4-dimethylamino pyridinium tetrafluoroborate (55, 56, etc.)). Other suitable techniques use carbodiimides, hydrazides, active esters, norborane, p-nitrobenzoic acid, N-hydroxysuccinimide, S—NHS, EDC, and TSTU (see also the introduction to reference [57]).

Linkages via a linker group may be made using any known procedure, for example, the procedures described in references [58-59]. One type of linkage involves reductive amination of the polysaccharide, coupling the resulting amino group with one end of an adipic acid linker group, and then coupling a protein to the other end of the adipic acid linker group [60-62]. Other linkers include B-propionamido [63], nitrophenyl-ethylamine [64], haloacyl halides [65], glycosidic linkages [66], 6-aminocaproic acid [67], ADH [68], C4 to C12 moieties [69], etc. As an alternative to using a linker, direct linkage can be used. Direct linkages to the protein may comprise oxidation of the polysaccharide followed by reductive amination with the protein, as described in, for example, references [70-72].

After conjugation, the level of unconjugated carrier protein may be measured. One way of making this measurement involves capillary electrophoresis [73] (e.g., in free solution), or micellar electrokinetic chromatography [74].

After conjugation, the level of unconjugated saccharide may be measured. One way of making this measurement involves HPAEC-PAD [75].

After conjugation, a step of separating conjugated saccharide from unconjugated saccharide may be used. One way of separating these saccharides is to use a method that selectively precipitates one component. Selective precipitation of conjugated saccharide is preferred, to leave unconjugated saccharide in solution, e.g, by a deoxycholate treatment [69].

After conjugation, a step of measuring the molecular size and/or molar mass of a conjugate may be carried out. In particular, distributions may be measured. One way of making these measurements involves size exclusion chromatography with detection by multiangle light scattering photometry and differential refractometry (SEC-MALS/RI) [76].

Conjugate Combinations

Saccharides prepared by the methods of the invention (in particular after conjugation as described above) can be mixed e.g. with each other and/or with other antigens. Thus the method of the invention may include the further step of mixing the saccharide with one or more further antigens. For example, conjugates from GBS type II obtained from the methods of the invention can be mixed with other streptococcal conjugates, such as GBS of other serogroups, e.g. Ia, Ib, III and/or V.

For example, the method of the invention may include a further step of mixing the type II GBS capsular saccharide obtained from the purification methods of the invention (and optionally conjugated to a carrier protein) with further antigens selected from the group consisting of: (i) a type Ia GBS capsular saccharide (and optionally conjugated to a carrier protein); (ii) a type Ib GBS capsular saccharide (and optionally conjugated to a carrier protein); (iii) a type III GBS capsular saccharide (and optionally conjugated to a carrier protein); and (iv) a type V GBS capsular saccharide (and optionally conjugated to a carrier protein). Preferably, the total quantity of GBS capsular saccharides in the composition is ≤70 μg. Preferably, the ratio of the masses of the GBS capsular saccharides is Ia:Ib:II:III:V=1:1:1:1:1. For example, each GBS capsular saccharide is present at 1-30 μg per unit dose (e.g. 5 μg, 10 μg or 20 μg per unit dose).

The composition will be produced by preparing separate conjugates (e.g. a different conjugate for each serotype) and then combining the conjugates.

Conjugates may be mixed by adding them individually to a buffered solution. A preferred solution is phosphate buffered physiological saline (final concentration 10 mM sodium phosphate). A preferred concentration of each conjugate (measured as saccharide) in the final mixture is between 1 and 20 μg/ml e.g., between 5 and 15 μg/ml, such as around 8 μg/ml. An optional aluminum salt adjuvant may be added at this stage (e.g., to give a final $Al^{3+}$ concentration of between 0.4 and 0.5 mg/ml).

After mixing, the mixed conjugates can be sterile filtered.

Pharmaceutical Compositions and Methods

The invention provides processes for preparing pharmaceutical compositions, comprising the steps of mixing (a) a saccharide of the invention (optionally in the form of a conjugate) with (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference [77].

The pharmaceutical compositions may be packaged into vials or into syringes. The syringes may be supplied with or without needles. A syringe will include a single dose of the composition, whereas a vial may include a single dose or multiple doses.

Aqueous compositions of saccharides of the invention are suitable for reconstituting other vaccines from a lyophilised form. Where a composition of the invention is to be used for such extemporaneous reconstitution, the invention provides a process for reconstituting such a lyophilised vaccine, comprising the step of mixing the lyophilised material with an aqueous composition of the invention. The reconstituted material can be used for injection.

Compositions may include an antimicrobial, particularly if packaged in a multiple dose format.

Compositions may comprise detergent, e.g., a Tween (polysorbate), such as TWEEN 80™. Detergents are generally present at low levels, (e.g., >0.01%).

Compositions may include sodium salts (e.g., sodium chloride) to give tonicity. A concentration of 10±2 mg/ml NaCl is typical.

Compositions will generally include a buffer. A phosphate buffer is typical.

Compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to around 6.1 prior to lyophilization.

Conjugates may be administered in conjunction with other immunoregulatory agents. In particular, compositions will usually include a vaccine adjuvant. Adjuvants which may be useful with compositions of the invention are known in the art.

Pharmaceutical Uses

The invention also provides a method of treating a patient, comprising administering the composition to the patient. The patient may either be at risk from the disease themselves or may be a pregnant woman (maternal immunization). The patient is preferably a human. The human can be of any age e.g., <2 years old, from 2-11 years old, from 11-55 years old, >55 years old, etc.

The invention also provides the composition for use in therapy. The invention also provides the use of the composition in the manufacture of a medicament for the treatment of disease. Preferably the disease is influenza or pneumonia.

Compositions will generally be administered directly to a patient. Direct delivery may be accomplished by parenteral injection (e.g., transcutaneously, subcutaneously, intraperitoneally, intravenously, intramuscularly, or to the interstitial space of a tissue), or by rectal, oral, vaginal, optical, transdermal, intranasal, ocular, aural, pulmonary or other mucosal administration. Intramuscular administration (e.g., to the thigh or the upper arm) is preferred. Injection may be via a needle (e.g., a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunization schedule and/or in a booster immunization schedule. A primary dose schedule may be followed by a booster dose schedule. Suitable timing between priming doses (e.g., between 4-16 weeks), and between priming and boosting, can be routinely determined.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition). The composition may be prepared for topical administration, e.g., as an ointment, cream or powder. The composition may be prepared for oral administration, e.g., as a tablet or capsule, or as a syrup (optionally flavored). The composition may be prepared for pulmonary administration, e.g., as an inhaler, using a fine powder or a spray. The composition may be prepared as a suppository or pessary.

The composition may be prepared for nasal, aural or ocular administration, e.g., as spray, drops, gel or powder (e.g., refs 143 & 144). Injectable compositions are preferred.

General

The term "comprising" encompasses "including" as well as "consisting" e.g. a composition "comprising" X may consist exclusively of X or may include something additional e.g. X+Y. The term, "consisting essentially of" means that the process, method or composition includes additional steps and/or parts that do not materially alter the basic and novel characteristics of the claimed process, method or composition. The term, "consisting of" is generally taken to mean that the invention as claimed is limited to those elements specifically recited in the claim (and may include their equivalents, insofar as the doctrine of equivalents is applicable).

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. For example, if a saccharide has already been partially purified by removing contaminating nucleic acids and/or proteins then this step can be omitted from the processes of the invention. Similarly, a step of removing contaminants can be performed to give material ready for detergent-mediated precipitation, but the precipitation need not be performed. The precipitation step need not be performed in order to fall within the scope of the invention, as the pre-precipitation material has utility as an intermediate in saccharide preparation, and may be used, stored, exported, etc. for later use e.g. for later precipitation. These different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

EXAMPLES

To illustrate the methods herein, *Streptococcus agalactiae* 18RS21, which produce serotype II capsular polysaccharides, isolated from patients with GBS disease, was studied.

Example 1

This example shows an exemplary purification protocol which provides much higher yields than have previously been possible for GBS type II polysaccharides.

Isolation and Purification of GBS Type II Polysaccharides

Figure 2:
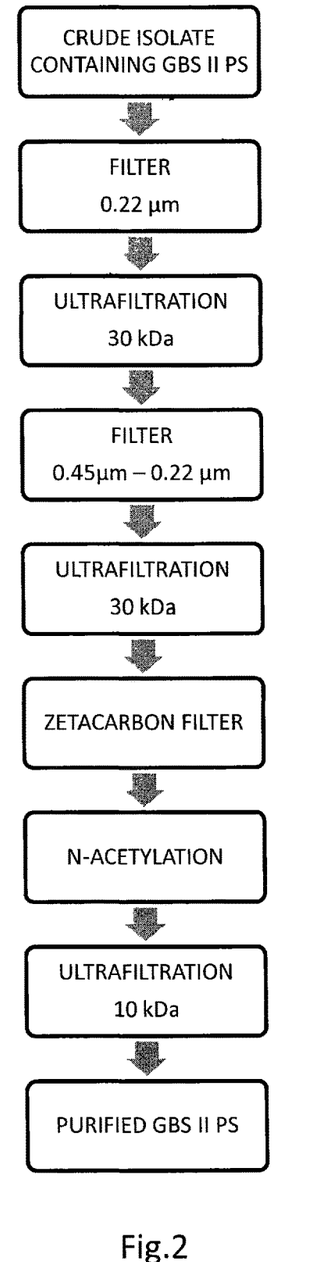
FIG. 2 shows a purification method for type II GBS capsular polysaccharide.

Native GBS type II polysaccharide were extracted and purified from bacteria using the process steps (see FIG. 2):

Bacterial Fermentation:

GBS type II strain was grown complex medium. Any method of culture may be used, though fermentative culture as disclosed herein is preferred.

Inactivation of Fermentation Biomass and Polysaccharide Extraction (Base Treatment):

If necessary, the biomass may be heated to bring it to room temperature. Sodium hydroxide (4 M) was added to the recovered biomass to a final concentration of 0.8 M and mixed to homogeneity. The suspension was subsequently incubated at 37° C. for 36 hours with mixing.

Neutralization of Biomass:

After extraction with base treatment, TRIS-base 1 M was added to a final concentration of 50 mM and the suspension was mixed to homogeneity. The pH of the mixture was adjusted to 7.8 with HCl (6 M) (1:1 dilution of the concentrated acid).

Alcohol Precipitation:

2 M CaCl was added to a final concentration of 0.1 M (52.6 mL per 1 L of neutralized mixture) and the suspension was mixed to homogeneity. Ethanol (96% (v/v)) was added to a final concentration of 30% (v/v) ethanol (428 mL per 1 L) and the suspension was mixed to homogeneity.

Tangential Microfiltration:

The mixture was diafiltered with 0.22 μm membrane (Hydrosart Sartorius) to remove the precipitate. First the biomass was concentrated to a work-volume=50-75 mL, then was diafiltered with buffer NaCl 1 M, TRIS 100 mM, $CaCl_2$ 100 mM, EtOH 30% (6 washing cycles).

First Tangential Diafiltration 30 kDa:

The material was dia-filtered on 30 kDa cellulose membrane (Sartorius Sartocon Hydrosart 0.1 $m^2$) against 16 volumes of TRIS 50 mM+NaCl 0.5 M buffered at pH 8.8 and then against 8 volumes of NaPi 10 mM buffered at pH 7.2.

AcONa:

Contaminant still present on the retentate were treated by precipitation adding AcONa 400 mM pH 4.4 (⅕ volume). The mixture was gently mixed for 15-20 minutes at room temperature and was filter sterilized using a 0.45/0.2 μm filter (Sartorius Sartobran filter). The material was then stored at 2-8° C. until needed (max 15 days).

Second Tangential Diafiltration 30 kDa:

The material was dia-filtered on 30 kDa cellulose membrane (Sartorius Sartocon Hydrosart 0.1 $m^2$) against 10 volumes of $Na_2CO_3$ 300 mM+NaCl 300 mM buffered at pH 8.8.

Filtration with a Protein Adherent Filter:

The material was passed through an activated carbon filter, (a ZetaCarbon™ filter from 3M) to remove residual protein contaminants.

Re-N-Acetylation of Polysaccharide:

Stock solution of acetic anhydride was prepared at the following proportions: 4.15 mL of acetic anhydride per L, with acetic anhydride:ethanol=1:1. Fresh acetic anhydride stock solution was added to the polysaccharide solution diluted to 2 mg/mL to a ratio of >22:1 acetic anhydride:polysaccharide repeating unit. The material was incubated with mixing for 2 hours at room temperature. The pH was checked at the end of 2 hours to verify that is was ~8.8.

Final Tangential Diafiltration 10 kDa:

The material was dia-filtered on 10 kDa cellulose membrane (Sartorius Sartocon Hydrosart 0.1 $m^2$) against 16 volumes of KPi 10 mM buffered at pH 7.2. Purified PSII was filtered 0.22 μm with disposable syringe filter (NALGENE®, PES) and store at +4/8° C.

Analytical Methods

Wet-chemical assays:

The saccharide content was determined by the sialic acid wet-chemical assay [78]. The sample was hydrolyzed in HCl at 80° C. 90 minutes, neutralized with NaOH and injected in a DIONEX™ system. Data are processed by CHROMELEON™ Software. The saccharides were eluted using a seven minute linear gradient of 90:10 to 60:40 0.1 M NaOH, 0.1 M NaAcetate:0.1 M NaOH, 0.5 M $NaNO_3$ on a CarboPac PA1 column with PA1 guard at a flow rate of 1.0 ml/min. Free sialic acid was determined by injecting the polysaccharide sample solubilized in water at 1.0 mg/ml without hydrolyzing the sample. In this way it was possible to separate free from bound sialic acid. In the polysaccharide sample, free sialic acid is not detected. The peak in the regeneration step was the polysaccharide not hydrolyzed. Free sialic acid is an important parameter because it is related with immune response.

The residual protein content was determined by a MicroBCA™ commercial kit (Pierce). The residual nucleic acid content was determined following the method published in Reference 79.

The residual Group B polysaccharide content was determined by determining the rhamnose residues and using a method based on HPAEC-PAD analysis. Rhamnose is a specific saccharide in the group B carbohydrate that is not found in the type polysaccharides and it was used to determine the concentration of contaminant carbohydrate residue after capsular polysaccharide purification. Samples and standards were hydrolyzed in TFA 2N at 100° C. for 3.0 hours, then evaporated in SpeedVac and reconstituted with 450 μl of $H_2O$. Rhamnose standard curve range is 1.0-10.0 μg/ml. The chromatographic conditions were: a CarboPac PA1 column with PA1 guard with a flow rate of 1.0 ml/min of NaOH 12 mM for 15 minutes followed by 5 minutes of regeneration with NaOH 500 mM and then re-equilibration in NaOH 12 mM for 25 minutes.

Results and Discussion

The new purification method (FIG. 2) provides improvements for purifying type II polysaccharides from GBS. Compared to the prior art method where a 30 kDa cellulose membrane is used in the final filtration step, the new purification method recovers much higher yield, whilst all the main potential contaminants (proteins, nucleic acids and Group B polysaccharide) remain low (compare rows "post N-acetylation ret UF 30K" and "post N-acetylation perm UF30K and ret 10K pool" in Table 1, page 25). The new purification method can be used for manufacturing of clinical and commercial materials derived from these capsular polysaccharides.

The new purification method also provides reproducible yields (Table 2), identity, conformity and purity (Table 3) at each purification step between different lots.

TABLE 2

The yield between different lots at each step of the purification method.

| Purification steps | Step Yield % | | |
|---|---|---|---|
| | Lot.EB1 | Lot.EB2 | Lot.EB4 |
| 1° UF 0.22 μm | — | — | — |
| 2° UF 30 kDa | 67.0 | 58.8 | 57.8 |
| 3° UF 30 kDa | 78.0 | 89.8 | 95.8 |
| Zeta Carbon | 77.4 | 68.9 | 65.4 |
| 4° UF 10 kDa | 103.3 | 113.3 | 112.8 |

TABLE 3

The identity, conformity and purity between different lots using the purification method of the invention.

| Lot. | Protein % w/w | Nucleic acid % w/w | Endotox EU/μg | PS group % w/w | Free sialic acid % w/w | MW | Sialic acid % mol/mol | NAc % mol/mol |
|---|---|---|---|---|---|---|---|---|
| EB1 | 0.10 | 0.02 | 0.002 | <0.01 | <0.16 | 424.9 | 99 | 104 |
| EB2 | 0.10 | 0.06 | 0.003 | <0.01 | <0.22 | 381.5 | 101 | 101 |
| EB4 | 0.10 | 0.02 | 0.020 | 0.03 | <0.19 | 338.5 | 99 | 100 |

Example 2

The relative molecular weight and particle size of Type II GBS capsular polysaccharide were investigated. The particle sizes of type Ia, Ib, III and V GBS capsular polysaccharides were also determined.

Analytic Methods

NMR Analysis:

Samples of purified polysaccharides were prepared by dissolving the powder in 1 mL of deuterium oxide ($D_2O$, Aldrich) to a uniform concentration. Aliquots (750 μL) of the samples were transferred to 5-mm NMR tubes (Wilmad). $^1H$ NMR experiments were recorded at 25° C. on Bruker 600 MHz spectrometer, and using 5-mm broadband probe (Bruker). For data acquisition and processing, XWINNMR software package (Bruker) was used. 1-D proton NMR spectra were collected using a standard one-pulse experiment with 32 scans. The transmitter was set at the HDO frequency (4.79 ppm). $^1H$ NMR spectra were obtained in quantitative matter using a total recycle time to ensure a full recovery of each signal (5× Longitudinal Relaxation Time $T_1$).

2-D homo- and helero-correlation NMR spectrum were recorded to assign the 1-D proton NMR profiles. The peak assignment was also confirmed by comparison with published data [80].

Static Light Scattering (MALLS):

This technique determines the root mean square (RMS) radius or "radius of gyration" Rg of a molecule. This is the mass averaged distance of each center of scattering from the molecule center of gravity. This method takes into account the averaged scattered light intensity, and is solvent and time-independent (see Ref. 81).

Dinamic Light Scattering (DLS):

This technique measures the hydrodynamic radius, Rh, of a molecule. This is the radius of a sphere with the same diffusion coefficient as the molecule. This method takes into account the fluctuations in scattered light intensity, and is time and solvent viscosity dependent (see Ref. 81).

Results and Discussion

The average molecular weight for the type II GBS capsular polysaccharide, estimated by Size Exclusion Chromatography, was ~270-420 kDa (Table 4). The structural identity of GBS type II capsular polysaccharides was confirmed by $^1H$ NMR spectroscopy (data not shown).

TABLE 4

Molecular weight of type II GBS capsular polysaccharide.

| Sample | $Log_{10}MW$ | MW (kDa) |
|---|---|---|
| 1 | 5.433 | 271.0 |
| 2 | 5.480 | 301.9 |
| 3 | 5.628 | 424.9 |

TABLE 4-continued

Molecular weight of type II GBS capsular polysaccharide.

| Sample | $Log_{10}MW$ | MW (kDa) |
|---|---|---|
| 4 | 5.581 | 381.5 |
| 5 | 5.579 | 379.3 |
| 6 | 5.530 | 338.5 |
| 8 | 5.618 | 414.5 |
| 9 | 5.467 | 292.8 |

The particle size measurements are provided in Table 5 below. In compact objects, the mass is close in to the center of mass. Rg is smaller than Rh and Rg/Rh<1. For an extended object, Rg is strongly influenced by the outlying masses but the hydrodynamic radius Rh is less strongly influenced. The ratio of Rg to Rh increases as the object becomes less compact (Rg/Rh>1).

TABLE 5

Particle sizes of the GBS capsular saccharides determined by MALLS and DLS.

| | dn/dc | MW (kDa) | Radius of gyration Rg (nm) | Hydrodynamic Radius Rh (nm) | Rg/Rh |
|---|---|---|---|---|---|
| GBS PS Ia | 0.113 | 335 | 47.5 | 8.8* | 5.40* |
| GBS PS Ib | 0.102 | 282 | 38.9 | n.d. | n.d. |
| GBS PS II | 0.139 | 240 | 26.5 | 23.4 (TD 18.9) | 1.13 (TD 1.40) |
| GBS PS III | 0.100 | 174 | 38.3 | n.d. | n.d. |
| GBS PS V | 0.110 | 172 | 27.2 | 151.3* (TD 63.2) | 0.18* (TD 0.43) |

Type II GBS capsular polysaccharide, purified from bacterial growth of 18RS21 strain, showed a hydrodynamic radius (apparent MW in size exclusion chromatography of flow through a filtration membrane) lower than the value expected considering its absolute MW (>200 kDa as estimated by SEC-MALLS analysis).

The unusual behavior of type II GBS capsular saccharide as compared with the other GBS types capsular saccharide (i.e. Ia, Ib, III and V), is probably due to the different arrangement of monosaccharides constituting the repeating unit. As example, while for type Ia and Ib GBS capsular saccharide the branch is composed three monosaccharides (out of the five sugars totally contained), for type II GBS capsular saccharide the branch contains one monosaccharides only. The shorter branch probably confers a more linear conformation and consequently a reduced steric hindrance.

Summary

The final Tangential Flow Filtration step of the conventional protocol for purifying GBS capsular saccharides is usually conducted by a 30 kDa cut-off filter (e.g see Ref. 2).

The inventors determined the average molecular weight for the type II GBS capsular polysaccharide to be ~270-420 kDa, so it was expected that this capsular polysaccharide would be retained by a 30 kDa filter. However, as shown in Example 1, surprisingly a large amount (~50%) of the type II GBS capsular polysaccharide passed through the 30 kDa filter in the final Tangential Flow Filtration step of the purification protocol (Table 1). The inventors surprisingly found that the type II GBS capsular polysaccharide has a lower hydrodynamic radius compared to the other GBS types capsular saccharide (i.e. Ia, Ib, III and V). Hence, replacing the filter in the final Tangential Flow Filtration step of the conventional purification protocol with a lower MW cut-off filter, e.g. by a 10 kDa cut-off filter is particularly advantageous for retaining the type II GBS capsular polysaccharide. The method of the invention therefore provides a higher yield of the type II GBS capsular polysaccharide.

It will be understood that the invention has been described by way of example only and modifications may be made whilst remaining within the scope and spirit of the invention.

REFERENCES

[1] Ada & Isaacs (2003) *Clin Microbiol Infect* 9:79-85.
[2] WO 2009/081276.
[3] Deng et al. (2000) *J Biol Chem* 275:7497-04.
[4] Paoletti et al. (1992) *Infect Immun* 60:4009-14
[5] Lewis et al. (2004) *PNAS USA* 101:11123-8.
[6] WO98/32873.
[7] Frash (1990) p. 123-145 of *Advances in Biotechnol. Processes* vol. 13 (eds. Mizrahi & VanWezel).
[8] EP 0072513.
[9] WO 2006/082527.
[10] U.S. Pat. No. 6,248,570.
[11] Baker et al. (2004)*J Infect Dis* 189:1103-12.
[12] Ramsay et al. (2001) *Lancet* 357(9251):195-196.
[13] Lindberg (1999) *Vaccine* 17 Suppl 2:S28-36.
[14] Buttery & Moxon (2000) *J R Coll Physicians Lond* 34:163-68.
[15] Ahmad & Chapnick (1999) *Infect Dis Clin North Am* 13:113-33, vii.
[16] Goldblatt (1998) *J. Med. Microbiol.* 47:563-7.
[17] European patent 0477508.
[18] U.S. Pat. No. 5,306,492.
[19] WO 98/42721.
[20] Dick et al. in *Conjugate Vaccines* (eds. Cruse et al.) Karger. Basel, 1989, 10:48-114.
[21] Hermanson *Bioconjugae Techniques*, Academic Press, San Diego (1996) ISBN: 0123423368.
[22] Ada & Isaacs (2003) *Clin Microbiol Infect* 9:79-85.
[23] Paoletti et al. (1990) *J Biol Chem* 265:18278-83.
[24] Wessels et al. (1990) *J Clin Invest* 86:1428-33.
[25] Paoletti et al. (1992)*J Clin Invest* 89:203-9.
[26] Wessels et al. (1987) *Proc Natl Acad Sci USA* 84:9170-4.
[27] Wang et al. (2003) *Vaccine* 21:1112-7.
[27] Wessels et al. (1995) *J Infect Dis* 171:879-84.
[28] Wessels et al. (1993) *Infect Immun* 61:4760-6.
[29] U.S. Pat. No. 4,356,170.
[30] Paoletti & Kasper (2003) *Expert Opin Biol Ther* 3:975-84, [31]WO 2006/082530.
[31] WO 2006/082530
[32] Anonymous (January 2002) *Research Disclosure,* 453077.
[33] Anderson (1983) *Infect Immun* 39(1):233-8.
[34] Anderson et al. (1985) *J Clin Invest* 76(1):52-9.
[35] EP-A-0372501.
[36] EP-A-0378881.
[37] EP-A-0427347.
[38] WO 93/17712
[39] WO 94/03208.
[40] WO98/58668.
[41] EP-A-0471177.
[42] WO 91/01146.
[43] Falugi et al. (2001) *Eur J Immunol* 31:3816-24.
[44] Baraldo et al. (2004) *Infect Immun* 72(8):4884-7.
[45] EP-A-0594610.
[46] WO 00/56360.
[47] WO 02/091998.
[48] Kuo et al. (1995) *Infect Immun* 63:2706-13.
[49] WO 01/72337
[50] WO 00/61761.
[51] WO 2004/018646.
[52] WO 99/42130.
[53] WO 2004/011027.
[54] WO 96/40242.
[55] Lees et al. (1996) Vaccine 14:190-98.
[56] WO 95/08348.
[57] WO 98/42721.
[58] U.S. Pat. No. 4,882,317.
[59] U.S. Pat. No. 4,695,624.
[60] EP 0477508.
[61] Porro et al. (1985) *Mol. Immunol.* 22:907-19.
[62] EP 0208375A.
[63] WO 00/10599.
[64] Gever et al. *Med. Microbiol. Immunol.,* 165:171-288 (1979).
[65] U.S. Pat. No. 4,057,685.
[66] U.S. Pat. No. 4,673,574; U.S. Pat. No. 4,761,283; U.S. Pat. No. 4,808,700.
[67] U.S. Pat. No. 4,459,286.
[68] U.S. Pat. No. 4,965,338.
[69] U.S. Pat. No. 4,663,160.
[70] U.S. Pat. No. 4,761,283.
[71] U.S. Pat. No. 4,356,170.
[72] WO 2012/035519
[73] Lamb et al. (2000) *Dev. Biol. (Basel)* 103:251-58.
[74] Lamb et al. (2000) Journal of Chromatography A 894:311-18.
[75] Lei et al. (2000) Dev. Biol. (Basel) 103: 259-64
[76] D'Ambra et al. (2000) Dev. Biol. (Basel) 103:241-42.
[77] Gennaro (2000) *Remington: The Science and Practice of Pharmacy.* 20th edition, ISBN: 0683306472.
[78] Svennerholm, L. *Biochem. Biophys. Acta* 1957, 24, 604.
[79] Sheldon, E. L.; et al. *Biochem. Biophys. Res. Comm.* 1989, 156(1), 474.
[80] Michon, F.; Chalifour, R.; Feldman, R.; Wessels, M.; Kasper. D. L.; Gamian. A.; Pozsgay, V.; Jennings. H. J. *Infect Immun* 1991, 59, 1690 and related papers.
[81] Jones C. *Anais da Academia Brasileira de Ciências* (2005) 77(2): 293-324 (Annals of the Brazilian Academy of Sciences).

TABLE 1

Characterisation at each step of the purification method of Example 1.

| sample | GBS PSII mg Sialic acid (cf = 0.233) Resorcinol assay | Sialic acid (cf = 0.233) HPAEC-PAD assay | Galactose (cf = 0.407) HPAEC-PAD assay | Step yield % SA HPAEC-PAD assay | Step yield % Gal HPAEC-PAD assay | GBS group PS % sacch based on SA | GBS group PS % sacch based on Gal | Free SA % SA HPAEC-PAD assay | Protein % BCA assay | Nucleic Acid % Abs (260 nm) assay | N-Acetylation % NMR assay |
|---|---|---|---|---|---|---|---|---|---|---|---|
| post 0.65 μm | NA | 2398.6 | NA | NA | NA | 93.8 | NA | NA | NA | NA | NA |
| post 0.45 μm | 2064.7 | 2286.0 | 1827.0 | 95.0 | NA | 89.2 | 111.6 | NA | NA | NA | NA |
| post 1° UF30K | 1311.8 | 1093.9 | 950.4 | 48.0 | 52.0 | NA | NA | NA | 1.0 | <0.1 | 79.6 |
| post 2° UF30K | 1344.7 | 1105.0 | 1074.8 | 101.0 | 113.0 | 0.1 | 0.1 | NA | 0.4 | <0.1 | 79.6 |
| post Z Carbon | 1147.6 | 998.6 | 868.8 | 90.0 | 81.0 | <0.2 | <0.2 | NA | NA | <0.1 | 79.2 |
| post N-acetylation ret UF30K | 524.5 | 475.1 | 426.1 | 48.0 | 49.0 | <0.1 | <0.1 | <2.2 | 0.7 | ND | >99.0 |
| post N-acetylation perm UF30K | not done | 451.2 | 444.2 | 45.0 | 51.0 | ND | ND | ND | ND | ND | >99.0 |
| post N-acetylation perm UF30K and ret 10K pool | 1125.8 | 870.8 | 825.9 | 87.0 | 95.0 | 0.07 | 0.07 | Ongoing | 0.12 | <0.1 | >99.0 |

The invention claimed is:

1. A method for purifying a type II Group B *Streptococcus* (GBS) capsular polysaccharide, comprising the following steps: (i) a microfiltration step that uses a ≤0.65 μm membrane; (ii) a filtration step that uses a membrane with a cut-off of less than about 30 kDa; (iii) a filtration step that uses a 0.45-0.22 μm membrane; (iv) a filtration step that uses a membrane with a cut-off of less than about 30 kDa; (v) a filtration step that uses a protein adherent filter; (vi) a filtration step that uses a membrane with a cut-off of about 10 kDa; (vii) a microfiltration step that uses a 0.22 μm disposable syringe filter.

2. The method of claim 1, wherein at least one of the filtration steps results in diafiltration.

3. The method of claim 1, wherein at least one of the filtrations is cross-flow or tangential flow.

4. The method of claim 1, wherein at least one of the filtration steps uses a cellulose membrane.

5. The method of claim 1, wherein at least one of the filtration steps uses a membrane with a cut-off of <25 kDa.

6. The method of claim 1, wherein at least one of the filtration steps uses a membrane with a cut-off of about 10 kDa.

7. The method of claim 1 comprising additional steps, said additional steps comprising: (a) providing a crude isolate containing the capsular polysaccharide; and (b) contacting the crude isolate with an alcohol solution and removing resulting precipitate.

8. The method of claim 1, further comprising precipitating the purified capsular polysaccharide.

9. The method of claim 1, further comprising conjugating the purified capsular polysaccharide to a carrier protein.

10. The method of claim 1, further comprising formulating a vaccine with the purified capsular polysaccharide as a component.

11. The method of claim 1, further comprising mixing said purified capsular polysaccharide with one or more capsular polysaccharide(s) from a GBS serotype selected from the group consisting of: Ia, Ib, III, IV, V, VI, VII and VIII.

12. The method of claim 1, wherein each filtration step uses a different buffer.

13. The method of claim 12, wherein the buffers are selected from a buffer comprising NaPi, a buffer comprising $Na_2CO_3$, and a buffer comprising KPi.

14. The method of claim 1, wherein step (iii) comprises adding AcONa.

15. The method of claim 1, wherein step (v) uses a carbon protein adherent filter.

16. The method of claim 1, wherein re-N-acetylation of the polysaccharide is performed before the final filtration step that uses a membrane with a cut-off of less than about 30 kDa.

* * * * *